(12) United States Patent
Bohlin

(10) Patent No.: US 7,566,788 B2
(45) Date of Patent: Jul. 28, 2009

(54) CRYSTALLINE FORMS

(75) Inventor: Martin Bohlin, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/689,864

(22) Filed: Mar. 22, 2007

(65) Prior Publication Data

US 2007/0225346 A1    Sep. 27, 2007

Related U.S. Application Data

(60) Provisional application No. 60/785,326, filed on Mar. 23, 2006.

(51) Int. Cl.
  A01N 43/50    (2006.01)
  C07D 235/00   (2006.01)
(52) U.S. Cl. .................... 548/304.4; 514/394
(58) Field of Classification Search ............ None
   See application file for complete search history.

(56) References Cited

U.S. PATENT DOCUMENTS

| | | | |
|---|---|---|---|
| 5,482,956 A | 1/1996 | Lunkenheimer et al. | |
| 6,166,219 A | 12/2000 | Yamasaki et al. | |
| 6,348,032 B1 | 2/2002 | Sperl et al. | |
| 6,352,985 B1 | 3/2002 | Yamasaki et al. | |
| 6,376,515 B2 | 4/2002 | Zhu et al. | |
| 6,534,535 B1 | 3/2003 | Zhu et al. | |
| 6,632,815 B2 | 10/2003 | Zhu et al. | |
| 6,686,368 B1 | 2/2004 | Zhu et al. | |
| 6,720,317 B1 | 4/2004 | Zhu et al. | |
| 6,835,739 B2 | 12/2004 | Zhu et al. | |
| 6,844,367 B1 | 1/2005 | Zhu et al. | |
| 7,030,139 B2 | 4/2006 | Cheng et al. | |
| 7,115,645 B2 | 10/2006 | Halfbrodt et al. | |
| 2002/0082280 A1 | 6/2002 | Sperl et al. | |
| 2006/0052421 A1 | 3/2006 | Welter et al. | |
| 2006/0094750 A1 | 5/2006 | Kon-I et al. | |
| 2006/0264490 A1* | 11/2006 | Page et al. ............ | 514/394 |
| 2007/0072853 A1 | 3/2007 | Liu et al. | |
| 2007/0082899 A1 | 4/2007 | Page et al. | |

FOREIGN PATENT DOCUMENTS

| | | |
|---|---|---|
| EP | 0597304 B1 | 1/2001 |
| EP | 0583665 B1 | 3/2003 |
| EP | 1403255 A1 | 3/2004 |
| FR | 5354 M | 9/1967 |
| FR | 1604908 | 6/1972 |
| WO | 9411349 A1 | 5/1994 |
| WO | 9411350 A1 | 5/1994 |
| WO | 9724334 A1 | 7/1997 |
| WO | 0112600 A1 | 2/2001 |
| WO | 0119798 A2 | 3/2001 |
| WO | 0151473 A1 | 7/2001 |
| WO | 0200651 A2 | 1/2002 |
| WO | 0246168 A2 | 6/2002 |
| WO | 02085866 A1 | 10/2002 |
| WO | 2004085385 A2 | 10/2004 |
| WO | 2004108688 A1 | 12/2004 |
| WO | 2004108712 A1 | 12/2004 |
| WO | 2005007625 A2 | 1/2005 |
| WO | 2005021547 A2 | 3/2005 |
| WO | 2005030732 A1 | 4/2005 |
| WO | 2005030733 A1 | 4/2005 |
| WO | 2005030761 A1 | 4/2005 |
| WO | 2005030762 A1 | 4/2005 |
| WO | 2005113542 A2 | 12/2005 |
| WO | 2006009876 A2 | 1/2006 |
| WO | 2006012642 A2 | 2/2006 |
| WO | 2006033627 A1 | 3/2006 |
| WO | 2006033628 A1 | 3/2006 |
| WO | 2006033629 A1 | 3/2006 |
| WO | 2006033630 A1 | 3/2006 |
| WO | 2006033631 A1 | 3/2006 |
| WO | 2006033632 A1 | 3/2006 |
| WO | 2006033633 A1 | 3/2006 |
| WO | 2006048754 A1 | 5/2006 |
| WO | 2006078941 A2 | 7/2006 |

OTHER PUBLICATIONS

Brittain et al. "Effects of pharmaceutical processing on drug polymorphs and solvates" in Polymorphism in Pharmaceutical Solids, vol. 95, p. 331-361.*
Express-Pharma-Online (http://www.expresspharmaonline.com/20031023/edit02.shtml).*
Chawla et al., "Challenges in Polymorphism of Pharmaceuticals", CRIPS vol 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Non-Final Office Action issued for U.S. Appl. No. 11/419,603 on Dec. 12, 2007.
Interview Summary issued for U.S. Appl. No. 11/419,603 on Mar. 18, 2008.
Evans et al., "Synthesis of a group of 1H-benzimidazoles and their screening for antiinflammatory activity," Eur J Med Chem, 1996, vol. 31, pp. 635-642, example 27.
Holenz et al., "Medicinal chemistry driven approaches toward novel and selective serotonin 5-HT6 receptor ligands," J. Med. Chem., 2005, vol. 48, pp. 1781-1795, table 1, compound 16, abstract.
Li et al., "Benzimidazole derivatives as novel nonpeptide luteinizing hormone-releasing hormone (LHRH) antagonists. Part 2: Benzimidazole-5-sulfonamides," Bioorganic & Medicinal Chemistry Letters, 2005, 15(3), pp. 805-807.

(Continued)

Primary Examiner—Golam M. M. Shameem
Assistant Examiner—Sun Jae Y Loewe
(74) Attorney, Agent, or Firm—Jianzhong Shen

(57) ABSTRACT

A salt of the compound N-{2-tert-butyl-1-[(4,4-difluorocyclohexyl)methyl]-1H-benzimidazol-5-yl}ethanesulfonamide, which is an ethanesulphonic acid salt, a sulphuric acid salt, an ethane disulphonic acid salt, a hydrochloric acid salt, a hydrobromic acid salt, a phosphoric acid salt, an acetic acid salt, a fumaric acid salt, a maleic acid salt, a tartaric acid salt, a citric acid salt, a methanesulphonic acid salt, or a p-toluenesulphonic acid salt of said compound.

3 Claims, 2 Drawing Sheets

OTHER PUBLICATIONS

STN International, File CAPLUS, accession No. 1972:419030, doc. No. 77:19030, Koshienko et al., "Benzo(1,2-d:3,4-d')diimidazole derivatives. II. Behavior of 3,6-dimethyl-and 3,6,7-trimethylbenzo(1,2-d:3,4-d')diimidazole toward nucleophilic agents," Khimiya Geterotsiklicheskikh Soedinenii, 1971, 7(8), pp. 1132-1135; XP002307925.

STN Intnl, File CHEMCATS, access No. 2003:1839419, "Benzenesulfonamide, N-(1,2-dimethyl-1H-benzimidazol-5-yl)-", CAS Reg No. 488708-12-9; & STN Intnl, File CHEMCATS, access No. 2003:2399372, "Benzenesulfonamide, N-(2-methyl-1-(phenylmethyl)-1H-benzimidazol-5-yl-", CAS Registry No. 488841-64-1; & STN Intnl, File CHEMCATS, access No. 2003:2595844, "Benzenesulfonamide, 4-methyl-N-(2-methyl-1-(phenylmethyl)-1H-benzimidazol-5-yl)-", CAS Reg No. 312617-94-0.

STN Intnl, File CHEMCATS, accession No. 2003:1839419, "Benzenesulfonamide, N-(1,2-dimethyl-1H-benzimidazol-5-yl)-" CAS Registry No. 488708-12-9; & STN Intnl, File CHEMCATS, accession No. 2003:1845322, "Benzenesulfonamide, 4-bromo-N-(1,2-dimethyl-1H-benzimidazol-5-yl)-", CAS Registry No. 489397-82-2; & STN Intnl. File CHEMCATS, accession No. 2003:2305521, "Benzenesulfonamide, N-(1,2-dimethyl-1H-benzimidazol-5-yl)-1-fluoro-", CAS Registry No. 503429-33-2.

STN Intnl, file Registry, see RN: 848855-83-4.

STN Intnl, File CAPLUS, accession No. 1975:408737, doc No. 83:8737, Bieksa, V. et al., "Relation of the reactivity of chloroethyl derivatives of 3,4-diaminobenzenesulfopiperidides to the structure of alkylating group", Lietuvos TSR Mokslu Akademijos Darbai, Serija B: Chemija, Technika, Fizine Geografija, (1974), (3) 91-8.

STN Intnl, File CAPLUS, accession No. 1973:515496, doc No. 79:115496, Bieksa, V. et al., "Chloroalkyl derivatives of benzimidazoles. 1. Chloroethyl derivatives of 2-methylbenzimidazole-5-sulfonamide," Lietuvos TSR Mokslu Akademijos Darbai, Serija B: Chemija, Technika, Fizine Geografija, (1973), (2), 93-103.

ISR issued for PCT/SE2007/000281 on Jul. 9, 2007.

English abstract for EP 0597304.

English abstract for FR 1604908.

English abstract for FR 5354M.

English abstract for WO 9411349.

English abstract for WO 9411350.

English abstract for WO 9724334.

English abstract for WO 0151473.

Non-Final Office Action issued for U.S. Appl. No. 11/419,603 on Jun. 23, 2008.

Final Rejection issued for U.S. Appl. No. 11/419,603 on Dec. 24, 2008.

Notice of Allowance issued for U.S. Appl. No. 11/419,603 on Mar. 10, 2009.

* cited by examiner

CRYSTALLINE FORMS

FIELD OF THE INVENTION

The present invention relates to novel salts of N-{2-tert-butyl-1-[(4,4-difluorocyclohexyl)methyl]-1H-benzimidazol-5-yl}ethanesulfonamide, which compound has the following formula:

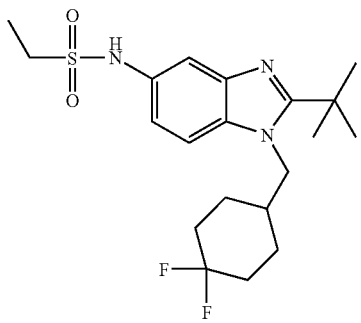

This compound is useful as a $CB_1$ receptor ligand, and may be useful in treating pain and/or other related symptoms or diseases. The invention also concerns pharmaceutical compositions which include the salts, as well as processes for the manufacture of the salts. The invention further concerns methods of treating medical conditions in which $CB_1$ receptors are implicated using the salts, for example pain, anxiety disorders, cancer, multiple sclerosis, Parkinson's disease, Huntington's chorea, Alzheimer's disease, gastrointestinal disorders and cardiovascular disorders, and the use of the salts in the manufacture of a medicament.

BACKGROUND OF THE INVENTION

In the formulation of drug compositions, it is important for the drug substance to be in a form in which it can be conveniently handled and processed. This is of importance, not only from the point of view of obtaining a commercially-viable manufacturing process, but also from the point of view of subsequent manufacture of pharmaceutical formulations comprising the active compound.

Further, in the manufacture of drug compositions, it is important that a reliable, reproducible and constant plasma concentration profile of drug is provided following administration to a patient.

Chemical stability, solid state stability, and "shelf life" of the active ingredients are also very important factors. The drug substance, and compositions containing it, should preferably be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

The skilled person will appreciate that, typically, if a drug can be readily obtained in a stable form, such as a stable crystalline form, advantages may be provided, in terms of ease of handling, ease of preparation of suitable pharmaceutical formulations, and a more reliable solubility profile.

WO 2005/030732 discloses a generic formula the scope of which encompasses N-{2-tert-butyl-1-[(4,4-difluorocyclohexyl)methyl]-1H-benzimidazol-5-yl}ethanesulfonamide.

A process for the synthesis of N-{2-tert-butyl-1-[(4,4-difluorocyclohexyl)methyl]-1H-benzimidazol-5-yl}ethanesulfonamide is described in Example 14 in WO 2006/033631.

BRIEF DESCRIPTION OF THE DRAWING(S)

FIG. 1 is an XRPD of the crystals of Example 3.
FIG. 2 is an XRPD of the crystals of Example 11.
FIG. 3 is an XRPD of the crystals of Example 13.
FIG. 4 is an XRPD of the crystals of Example 14.

DETAILED DESCRIPTION OF THE INVENTION

The present invention provides specific salts of N-{2-tert-butyl-1-[(4,4-difluorocyclohexyl)methyl]-1H-benzimidazol-5-yl}ethanesulfonamide.

More specifically, the present invention relates to a salt of the compound N-{2-tert-butyl-1-[(4,4-difluorocyclohexyl)methyl]-1H-benzimidazol-5-yl}ethanesulfonamide, which is an ethanesulphonic acid salt, a sulphuric acid salt, an ethane disulphonic acid salt, a hydrochloric acid salt, a hydrobromic acid salt, a phosphoric acid salt, an acetic acid salt, a fumaric acid salt, a maleic acid salt, a tartaric acid salt, a citric acid salt, a methanesulphonic acid salt, or a p-toluenesulphonic acid salt of said compound.

In one embodiment of the invention the salt is an ethane sulphonic acid salt, a sulphuric acid salt, or an ethane disulphonic acid salt of N-{2-tert-butyl-1-[(4,4-difluorocyclohexyl)methyl]-1H-benzimidazol-5-yl}ethanesulfonamide.

One embodiment of the invention relates to an ethane sulphonic acid salt of N-{2-tert-butyl-1-[(4,4-difluorocyclohexyl)methyl]-1H-benzimidazol-5-yl}ethanesulfonamide having an X-ray powder diffraction pattern with specific peaks at d-values at 14.0, 7.0, 4.99, and 4.62 Å, and/or essentially as defined in Table 1 and/or essentially as defined in FIG. 1.

Another embodiment of the invention relates to a sulphuric acid salt of N-{2-tert-butyl-1-[(4,4-difluorocyclohexyl)methyl]-1H-benzimidazol-5-yl}ethanesulfonamide having an X-ray powder diffraction pattern with specific peaks at d-values at 11.7, 11.3, 5.8, 5.6, 5.6, and 5.4 Å, and/or essentially as defined in Table 2 and/or essentially as defined in FIG. 2.

A further embodiment of the invention relates to an ethane disulphonic acid salt of N-{2-tert-butyl-1-[(4,4-difluorocyclohexyl)methyl]-1H-benzimidazol-5-yl}ethanesulfonamide having an X-ray powder diffraction pattern essentially as defined in FIG. 3.

A yet further embodiment of the invention relates to a maleic acid salt of N-{2-tert-butyl-1-[(4,4-difluorocyclohexyl)methyl]-1H-benzimidazol-5-yl}ethanesulfonamide having an X-ray powder diffraction pattern essentially as defined in FIG. 4.

The X-ray powder diffraction spectra for typical samples of the salts of the present invention are shown in the Figures hereinafter. It will be understood that the values of the X-ray powder diffraction pattern may vary slightly from one machine to another or from one sample to another, and so the values quoted are not to be construed as absolute.

According to a further aspect of the invention there is provided a salt of the invention in substantially crystalline form.

Although we have found that it is possible to produce salts of the invention in forms which are greater than 80% crystalline, by "substantially crystalline" we include greater than 20%, preferably greater than 30%, and more preferably greater than 40% (e.g. greater than any of 50, 60, 70, 80 or 90%) crystalline.

According to a further aspect of the invention there is also provided a salt of the invention in partially crystalline form. By "partially crystalline" we include 5% or between 5% and 20% crystalline.

The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The term "stability" as defined herein includes chemical stability and solid state stability.

By "chemical stability", we include that it may be possible to store salts of the invention in an isolated form, or in the form of a formulation in which it is provided in admixture with pharmaceutically acceptable carriers, diluents or adjuvants (e.g. in an oral dosage form, such as a tablet, capsule etc.), under normal storage conditions, with an insignificant degree of chemical degradation or decomposition.

By "solid state stability", we include that it may be possible to store salts of the invention in an isolated solid form, or in the form of a solid formulation in which it is provided in admixture with pharmaceutically acceptable carriers, diluents or adjuvants (e.g. in an oral dosage form, such as a tablet, capsule etc.), under normal storage conditions, with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably room temperatures, such as 15 to 30° C.), pressures of between 0.1 and 2 bars (preferably at atmospheric pressure), relative humidities of between 5 and 95% (preferably 10 to 60%), and/or exposure to 460 lux of UV/visible light, for prolonged periods (i.e. greater than or equal to six months). Under such conditions, salts of the invention may be found to be less than 15%, more preferably less than 10%, and especially less than 5%, chemically degraded/decomposed, or solid state transformed, as appropriate. The skilled person will appreciate that the above-mentioned upper and lower limits for temperature, pressure and relative humidity represent extremes of normal storage conditions, and that certain combinations of these extremes will not be experienced during normal storage (e.g. a temperature of 50° C. and a pressure of 0.1 bar).

A further aspect of the present invention comprises processes for the preparation of the salts. The precise conditions under which the salts are formed may be empirically determined. The salts may be obtained by crystallisation under controlled conditions.

One embodiment of the invention relates to a process for the preparation of a salt according to the present invention, which process comprises addition of the appropriate acid to a solution or slurry of N-{2-tert-butyl-1-[(4,4-difluorocyclohexyl)methyl]-1H-benzimidazol-5-yl}ethanesulfonamide in suitable solvent or liquid.

In one embodiment of the inventive process the appropriate acid is added to N-{2-tert-butyl-1-[(4,4-difluorocyclohexyl)methyl]-1H-benzimidazol-5-yl}ethanesulfonamide dissolved in a solvent selected from the group: acetates, lower alkyl alcohols, aliphatic and aromatic hydrocarbons, dialkyl ethers, dialkyl ketones, acetonitrile, chlorinated alkanes, aqueous solvents, or mixtures thereof.

In a further embodiment of the inventive process the solvent is selected from the group: $C_{1-6}$-alkyl acetates, linear or branched $C_{1-6}$-alkyl alcohols, $C_{6-12}$-aliphatic hydrocarbons, $C_{6-10}$-aromatic hydrocarbons, di-$C_{1-6}$-alkyl ethers, di-$C_{1-6}$-alkyl ketones, chlorinated methanes or ethanes, acetonitrile, water, or mixtures thereof.

In a yet further embodiment of the inventive process the solvent is selected from the group: ethyl acetate, iso-propyl acetate, methanol, ethanol, iso-propanol, n-heptane, diethyl ether, acetone, dichloromethane, water, or mixtures thereof.

In a further embodiment of the inventive process the solvent is selected from the group: ethyl acetate, methyl iso-butyl ketone, and iso-propyl acetate.

In another embodiment of the inventive process the appropriate acid is added to N-{2-tert-butyl-1-[(4,4-difluorocyclohexyl)methyl]-1H-benzimidazol-5-yl}ethanesulfonamide slurried in a liquid selected from the group: acetates, lower alkyl alcohols, aliphatic and aromatic hydrocarbons, dialkyl ethers, dialkyl ketones, acetonitrile, chlorinated alkanes, aqueous liquids, or mixtures thereof.

In a further embodiment of the inventive process the liquid is selected from the group: $C_{1-6}$ alkyl acetates, linear or branched $C_{1-6}$ alkyl alcohols, $C_{6-12}$ aliphatic hydrocarbons, $C_{6-10}$ aromatic hydrocarbons, di-$C_{1-6}$ alkyl ethers, di-$C_{1-6}$ alkyl ketones, chlorinated methanes or ethanes, acetonitrile, water, or mixtures thereof.

In a yet further embodiment of the inventive process the liquid is selected from the group: ethyl acetate, iso-propyl acetate, methanol, ethanol, iso-propanol, n-heptane, diethyl ether, acetone, dichloromethane, water, or mixtures thereof.

In a further embodiment of the inventive process the liquid is methyl tert-butyl ether.

Crystallisation temperatures and crystallisation times depend upon the salt that is to be crystallised, the concentration of that salt in solution, and the solvent system which is used.

Crystallisation may also be initiated and/or effected by way of standard techniques, for example with or without seeding with crystals of the appropriate crystalline salt of the invention.

One embodiment of the invention relates to a pharmaceutical formulation including a salt according to the present invention in admixture with a pharmaceutically acceptable adjuvant, diluent or carrier.

Another embodiment of the invention relates to a salt according to the present invention for use as a medicament.

A yet further embodiment of the invention relates to the use of a salt according to the present invention in the manufacture of a medicament for the therapy of pain.

One embodiment of the invention relates to the use of a salt according to any the present invention in the manufacture of a medicament for the treatment of anxiety disorders.

Another embodiment of the invention relates to the use of a salt according to the present invention in the manufacture of a medicament for the treatment of cancer, multiple sclerosis, Parkinson's disease, Huntington's chorea, Alzheimer's disease, gastrointestinal disorders and cardiovascular disorders.

A further embodiment of the invention relates to the use of a salt according to the present invention for the manufacture of a medicament for the treatment of gastroesophageal reflux disease (GERD).

A yet further embodiment of the invention relates to the use of a salt according to the present invention for the manufacture of a medicament for the treatment of functional gastrointestinal disorder (FGD).

One embodiment of the invention relates to the use of a salt according to the present invention for the manufacture of a medicament for the treatment of functional dyspepsia (FD).

Another embodiment of the invention relates to the use of a salt according to the present invention for the manufacture of a medicament for the treatment of irritable bowel syndrome (IBS).

A further embodiment of the invention relates to a method for the therapy of pain in a warm-blooded animal, comprising the step of administering to said animal in need of such therapy a therapeutically effective amount of a salt according to the present invention.

A yet further embodiment of the invention relates to a method for the treatment of pain, whereby a pharmaceutically and pharmacologically effective amount of a salt according to the present invention is administered to a subject in need of such treatment.

One embodiment of the invention relates to a method for the treatment of anxiety disorders, whereby a pharmaceutically and pharmacologically effective amount of a salt according to the present invention is administered to a subject in need of such treatment.

Another embodiment of the invention relates to a method for the treatment of cancer, multiple sclerosis, Parkinson's disease, Huntington's chorea, Alzheimer's disease, gastrointestinal disorders or cardiovascular disorders, whereby a pharmaceutically and pharmacologically effective amount of a salt according to the present invention is administered to a subject in need of such treatment.

A further embodiment of the invention relates to a method for the treatment of gastroesophageal reflux disease (GERD), whereby a pharmaceutically and pharmacologically effective amount of a salt a salt according to the present invention is administered to a subject in need of such treatment.

A yet further embodiment of the invention relates to a method for the treatment of functional gastrointestinal disorder, whereby a pharmaceutically and pharmacologically effective amount of a salt according to the present invention is administered to a subject in need of such treatment.

One embodiment of the invention relates to a method for the treatment of functional dyspepsia whereby a pharmaceutically and pharmacologically effective amount of a salt according to the present invention is administered to a subject in need of such treatment.

Another embodiment of the invention relates to a method for the treatment of irritable bowel syndrome (IBS), whereby a pharmaceutically and pharmacologically effective amount of a salt according to the present invention is administered to a subject in need of such treatment.

Biological Evaluation hCB$_1$ Receptor Binding

Human CB$_1$ receptor from Receptor Biology (hCB$_1$) are thawed at 37° C., passed 3 times through a 25-gauge blunt-end needle, diluted in the cannabinoid binding buffer (50 mM Tris, 2.5 mM EDTA, 5 mM MgCl$_2$, and 0.5 mg/mL BSA fatty acid free, pH 7.4) and aliquots containing the appropriate amount of protein are distributed in 96-well plates. The IC$_{50}$ of the salts of the invention at hCB$_1$ are evaluated from 10-point dose-response curves done with $^3$H-CP55,940 at 20000 to 25000 dpm per well (0.17-0.21 nM) in a final volume of 300 µl. The total and non-specific binding are determined in the absence and presence of 0.2 µM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM MgCl$_2$, 0.5 mg BSA pH 7.0). The filters are dried for 1 hour at 55° C. The radioactivity (cpm) is counted in a TopCount (Packard) after adding 65 µl/well of MS-20 scintillation liquid.

hCB$_1$ GTPγS Binding

Human CB$_1$ receptor from Receptor Biology (hCB$_1$) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM MgCl$_2$, pH 7.4, 0.1% BSA). The EC$_{50}$ and E$_{max}$ of the compounds of the invention are evaluated from 10-point dose-response curves done in 300 µl with the appropriate amount of membrane protein and 100000-130000 dpm of GTPg$^{35}$S per well (0.11-0.14 nM). The basal and maximal stimulated binding is determined in absence and presence of 10 µM (hCB$_1$) Win 55,212-2 respectively. The membranes are pre-incubated for 5 minutes with 112.5 µM (hCB$_1$) GDP prior to distribution in plates (30 µM (hCB$_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM MgCl$_2$, 50 mM NaCl, pH 7.0). The filters are dried for 1 hour at 55° C. The radioactivity (cpm) is counted in a TopCount (Packard) after adding 65 µl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki = IC_{50}/(1+[rad]/Kd),$$

Wherein IC$_{50}$ is the concentration of the compound of the invention at which 50% displacement has been observed; [rad] is a standard or reference radioactive ligand concentration at that moment; and Kd is the dissociation constant of the radioactive ligand towards the particular receptor.

Using the above-mentioned assays, the Ki towards human CB$_1$ receptors for certain substances of the invention are in the range of between 3 nM and 195 nM. EC$_{50}$ for these substances are in the range of between 2.3 nM and 300 nM. Emax for these substances are in the range of between 109% and 144%.

Screening for Compounds Active Against TLESR (GERD)

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. The infusion of the nutrient meal is followed by air infusion at a rate of 500 ml/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal ≦2 s before its onset in which case the relaxation is classified as swallow-induced. The pressure difference between the LES and the stomach should be less than 2 mmHg, and the duration of the complete relaxation longer than 1 s.

Screening for Compounds Active Against IBS

In this study the effect of acute administration of a compound on the visceromotor response to isobaric colorectal distension in rats is investigated (Ritchie J. Pain from distension of the pelvic colon by inflating a balloon in the irritable bowel syndrome. *Gut* 1973; 6: 105-112. Ness T J, Gebhart G F. Colorectal distension as a noxious visceral stimulus: physiological and pharmacological characterization of pseudoeffective reflexes in the rat. *Brain Research* 1988; 450: 153-169).

Methods

Colorectal distension (CRD) is performed in all rats (Sprague Dawley) using a paradigm of 12 consecutive distensions (or pulses) at 80 mmHg for 30 seconds each with 4.5 minute intervals (12×80 mmHg). The visceromotor response is determined by quantifying phasic changes in the balloon pressure, which is processed by specially designed computer software. The compound is dissolved in saline and administered at the doses of 1, 3 and 10 μmol/kg. The compound is given intravenously in a volume of 1 mL/kg between the third and fourth distension.

The invention will now be illustrated by the following non-limiting Example.

Figure 1:
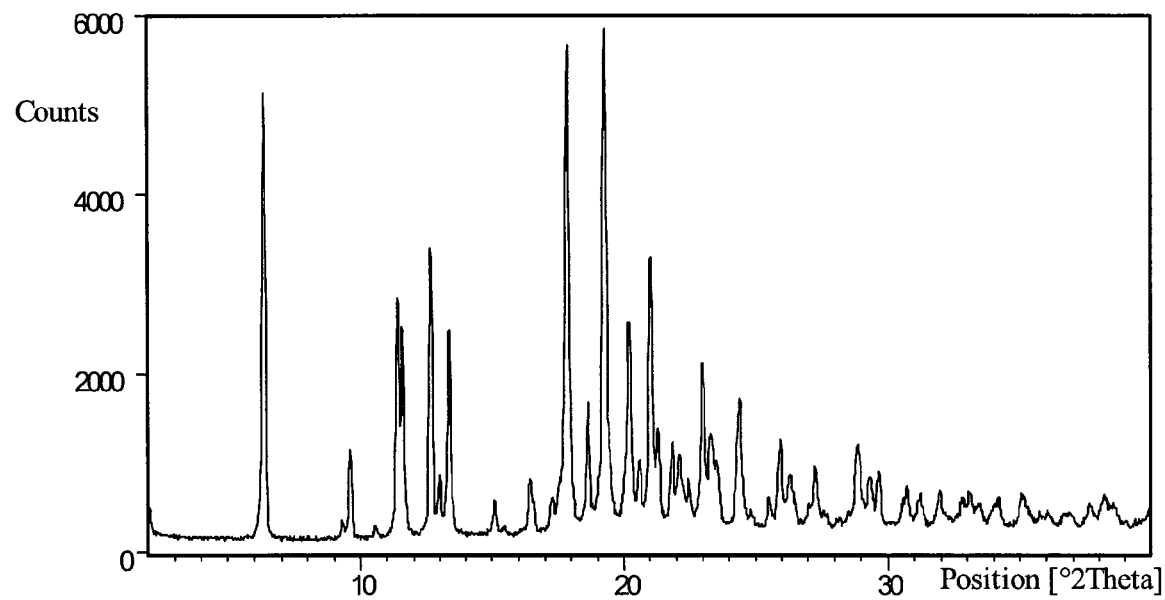
FIG. 1 shows an X-ray powder diffractogram for crystalline ethane sulphonic acid salt of N-{2-tert-butyl-1-[(4,4-difluorocyclohexyl)methyl]-1H-benzimidazol-5-yl}ethanesulfonamide.

X-ray powder diffraction analysis (XRPD) was performed using variable slits on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a PANalytical X'Pert PRO MPD diffractometer.

It will be appreciated by the skilled person that crystalline forms of compounds of the invention may be prepared by analogy with processes described herein and/or in accordance with the Examples below, and may show essentially the same XRPD diffraction patterns as those disclosed herein. By "essentially the same" XRPD diffraction patterns, we include those instances when it is clear from the relevant patterns (allowing for experimental error) that essentially the same crystalline form has been formed. When provided, XRPD distance values may vary in the range ±2 on the last given decimal place. It will be appreciated by the skilled person that XRPD intensities may vary when measured for essentially the same crystalline form for a variety of reasons including, for example, preferred orientation.

Preparation of N-{2-tert-Butyl-1-[(4,4-difluorocyclohexyl)methyl]-1H-benzimidazol-5-yl}ethanesulfonamide Step A N-(4-{[(4,4-Difluorocyclohexyl)methyl]amino}-3-nitrophenyl)acetamide

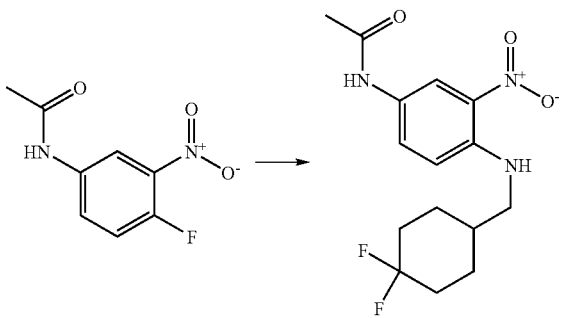

N-(4-Fluoro-3-nitrophenyl)acetamide (1.15 g, 5.84 mmol) and [(4,4-difluorocyclohexyl)methyl]amine hydrochloride (1.30 g, 7.59 mmol) were stirred in 30 mL of EtOH containing TEA (2.40 mL, 17.5 mmol) at 80° C. for 48h. The solvent was evaporated. The residue was dissolved in EtOAc and washed with aqueous 5% $KHSO_4$ solution, saturated aqueous $NaHCO_3$ solution, saturated aqueous NaCl solution and dried over anhydrous $Na_2SO_4$. The product was crystallized from EtOAc. The left over mother liquor was purified by silica gel flash chromatography using 2:1/hexanes:acetone as eluent. Yield: 1.50 g (78%). $^1$H NMR (400 MHz, CHLOROFORM-D) δ 1.33-1.47 (m, 2H), 1.66-1.77 (m, 2H), 1.77-1.86 (m, 1H), 1.89-1.93 (m, 1H), 1.93-1.97 (m, 1H), 2.10-2.17 (m, 2H), 2.18 (s, 3H), 3.23 (dd, J=6.74, 5.76 Hz, 2H), 6.83 (d, J=9.37 Hz, 1H), 7.15 (s, 1H), 7.80 (dd, J=9.18, 2.54 Hz, 1H), 8.09 (d, J=2.54 Hz, 2H).

Step B

N-(3-Amino-4-{[(4,4-difluorocyclohexyl)methyl]amino}phenyl)acetamide

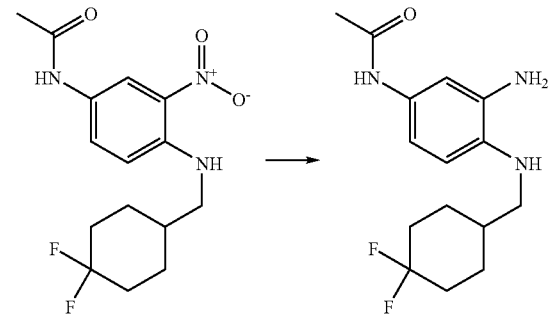

N-(4-{[(4,4-Difluorocyclohexyl)methyl]amino}-3-nitrophenyl)acetamide (1.48 g, 4.52 mmol) was dissolved in 50 mL of EtOAc containing a catalytic amount of 10% Pd/C. The solution was shaken in a Parr hydrogenation apparatus under $H_2$ atmosphere (45 psi) at rt for 24 h. The solution was filtered through Celite and the solvent was evaporated. Yield: 1.32 g (98%). $^1$H NMR (400 MHz, CHLOROFORM-D) δ 1.31-1.43 (m, 2H), 1.64-1.73 (m, 2H), 1.74-1.82 (m, 1H), 1.89-1.93 (m, 1H), 1.93-1.96 (m, 1H), 2.08-2.17 (m, 5H), 3.00 (d, J=6.64 Hz, 2H), 3.27-3.46 (m, 2H), 6.55 (d, J=8.40 Hz, 1H), 6.70 (dd, J=8.40, 2.34 Hz, 1H), 7.01 (s, 1H), 7.13 (d, J=2.34 Hz, 1H).

Step C

N-{2-tert-Butyl-1-[(4,4-difluorocyclohexyl)methyl]-1H-benzimidazol-5-yl}acetamide

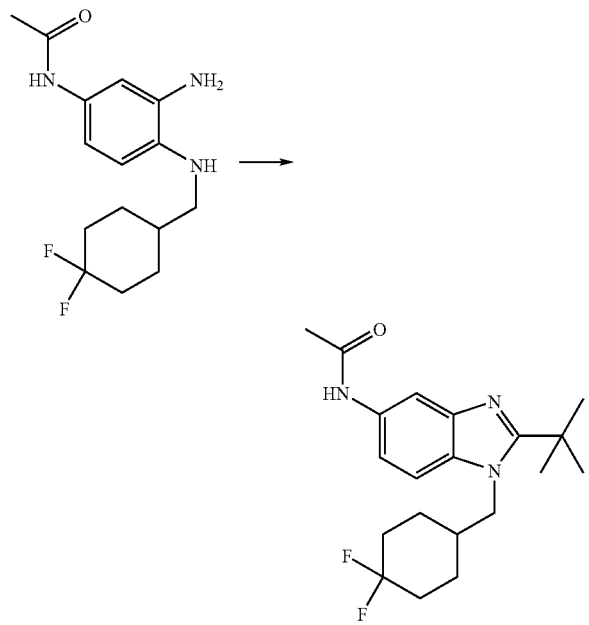

N-(3-Amino-4-{[(4,4-difluorocyclohexyl)methyl]amino}phenyl)acetamide (1.32 g, 4.44 mmol) was dissolved in 100 mL of DCM containing DMAP (108 mg, 0.89 mmol). Trimethylacetyl chloride (0.60 mL, 4.88 mmol) was added dropwise and the solution was stirred at rt for 2 h. The solution washed with saturated aqueous $NaHCO_3$ solution, saturated aqueous NaCl solution and dried over anhydrous $Na_2SO_4$. Part of the product precipitated during the washings and was filtered. The organic phase was evaporated and combined with the precipitate. The product was dissolved in 30 mL of AcOH and placed in 6 sealed tubes (5 mL/tube). Each tube was heated at 150° C. in a Personal Chemistry microwaves instrument for 2.5 h. The fractions were pooled and the solvent was evaporated. The product was dissolved in EtOAc and washed with aqueous $NaHCO_3$ solution, saturated aqueous NaCl solution and dried over anhydrous $Na_2SO_4$. The product was purified by silica gel flash chromatography using 2:1/acetone:hexanes as eluent. Yield: 1.11 g (68%). $^1$H NMR (400 MHz, METHANOL-$D_4$) δ 1.40-1.49 (m, 2H), 1.52 (s, 9H), 1.60-1.65 (m, 2H), 1.67-1.77 (m, 1H), 1.96-2.06 (m, 3H), 2.11 (s, 3H), 2.15-2.23 (m, 1H), 4.28 (d, J=7.62 Hz, 2H), 7.35-7.39 (m, 1H), 7.40-7.44 (m, 1H), 7.85 (d, J=1.76 Hz, 1H).

Step D 2-tert-Butyl-1-[(4,4-difluorocyclohexyl)methyl]-1H-benzimidazol-5-amine

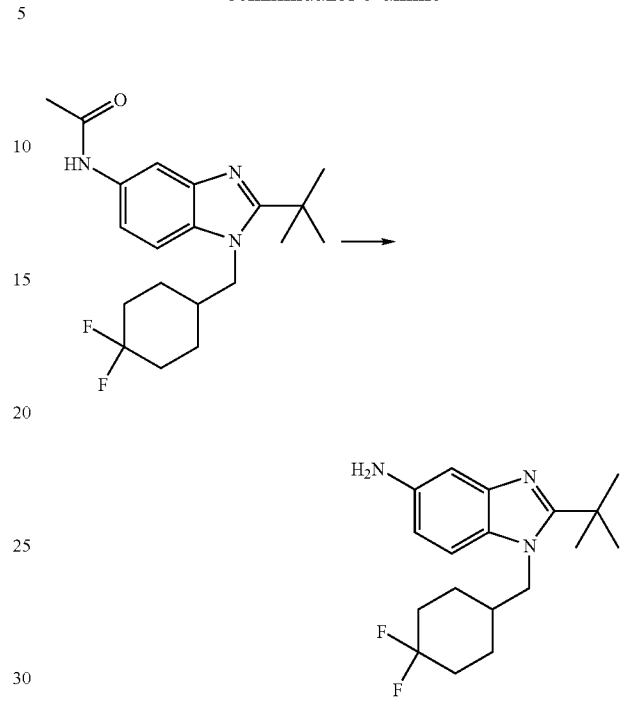

N-{2-tert-Butyl-1'-[(4,4-difluorocyclohexyl)methyl]-1H-benzimidazol-5-yl}acetamide (500 mg, 1.37 mmol) was dissolved in 10 mL of 1:1/EtOH:2M HCl. The solution was divided into two sealed tubes (5 mL/tube). Each tube was heated at 120° C. in a Personal Chemistry microwaves instrument for 1 h. The fractions were pooled and the solvent was evaporated. The residue was diluted with 2M NaOH and extracted (3×) with EtOAc. The organic phase washed with saturated aqueous NaCl solution and dried over anhydrous $Na_2SO_4$. The solvent was evaporated. Yield: 440 mg (99%). $^1$H NMR (400 MHz, CHLOROFORM-D) δ 1.40-1.52 (m, 2H), 1.52-1.54 (m, 9H), 1.56-1.66 (m, 4H), 1.68-1.75 (m, 2H), 2.07-2.17 (m, 3H), 4.14 (d, J=7.62 Hz, 2H), 6.65 (dd, J=8.50, 2.25 Hz, 1H), 7.04-7.09 (m, 2H).

Step E

N-{2-tert-Butyl-1-[(4,4-difluorocyclohexyl)methyl]-1H-benzimidazol-5-yl}ethanesulfonamide

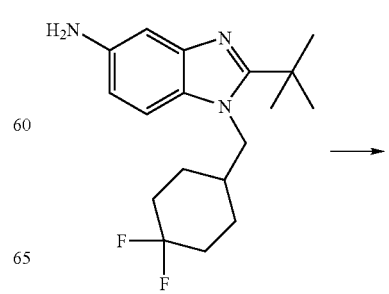

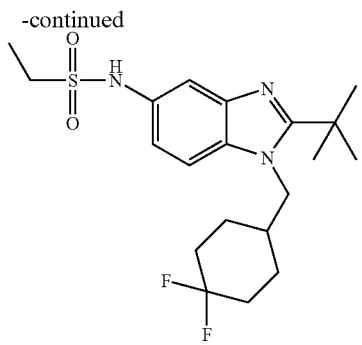

2-tert-Butyl-1-[(4,4-difluorocyclohexyl)methyl]-1H-benzimidazol-5-amine (440 mg, 1.37 mmol) and DMAP (165 mg, 1.37 mmol) were dissolved in 50 mL of DCM. Ethanesulfonyl chloride (0.170 mL, 1.78 mmol) was added dropwise and the solution was stirred at rt for 2.5 h. The solution washed with saturated aqueous NaHCO$_3$ solution, saturated aqueous NaCl solution and dried over anhydrous Na$_2$SO$_4$. The product was purified by silica gel flash chromatography using EtOAc as eluent. The fractions were concentrated and the residue was dissolved in 25 mL of MeOH. TFA (0.155 mL, 2.06 mmol) was added dropwise and the solution was stirred at rt for 30 min. The solvent was evaporated and the product was precipitated in ether affording the title compound as its corresponding TFA salt. Yield: 565 mg (78%). $^1$H NMR (400 MHz, METHANOL-D$_4$) δ 1.29 (t, J=7.42 Hz, 3H), 1.48-1.60 (m, 2H), 1.64 (s, 9H), 1.66-1.72 (m, 2H), 1.73-1.82 (m, 2H), 1.99-2.09 (m, 2H), 2.18-2.28 (m, 1H), 3.11 (m, 2H), 4.50 (d, J=7.62 Hz, 2H), 7.38 (dd, J=9.08, 2.05 Hz, 1H), 7.72 (d, J=2.15 Hz, 1H), 7.85 (d, J=8.98 Hz, 1H); MS (ESI) (M+H)$^+$ 414.0.

Preparation of Ethane Sulphonic Acid Salt of N-{2-tert-butyl-1-[(4,4-difluorocyclohexyl)methyl]-1H-benzimidazol-5-yl}ethanesulfonamide

EXAMPLE 1

N-{2-tert-butyl-1-[(4,4-difluorocyclohexyl)methyl]-1H-benzimidazol-5-yl}ethanesulfonamide (131 mg) was dissolved in ethyl acetate (1.3 ml) and ethane sulphonic acid (27 μl, 95%) was added. The mixture was heated to 55° C. to dissolve everything. Then, the solution was cooled down to room temperature and left to crystallise over night. The resulting slurry was filtered off and washed with ethyl acetate (0.5 ml) and dried shortly. The resulting product (150 mg) was crystalline N-{2-tert-butyl-1-[(4,4-difluorocyclohexyl)methyl]-1H-benzimidazol-5-yl}ethanesulfonamide esylate corresponding to a yield of approximately 94%.

EXAMPLE 2

N-{2-tert-butyl-1-[(4,4-difluorocyclohexyl)methyl]-1H-benzimidazol-5-yl}ethanesulfonamide (240 mg) was dissolved in ethyl acetate (2.4 ml) and ethane sulphonic acid (25 μl, 95%) was added. The mixture was heated to 50° C. and after a few minutes it started to crystallise. Then a second portion of ethane sulphonic acid (25 t, 95%) was added. The resulting slurry was cooled down to room temperature and left over night before it was filtered off and washed with ethyl acetate (1 ml) and dried under vacuum at 40° C. The resulting product (280 mg) was crystalline N-{2-tert-butyl-1-[(4,4-difluorocyclohexyl)methyl]-1H-benzimidazol-5-yl}ethanesulfonamide esylate.

EXAMPLE 3

N-{2-tert-butyl-1-[(4,4-difluorocyclohexyl)methyl]-1H-benzimidazol-5-yl}ethanesulfonamide (1.82 g) was dissolved in ethyl acetate (18.2 ml) at 40° C. To the clear solution, a first portion of ethane sulphonic acid (100 μl, 95%) was added. Crystallisation started immediately. After 20 minutes a second portion of acid was added (100 μl, 95%). The crystallisation was left for 30 minutes before a third portion of ethane sulphonic acid (178 μl, 95%) was added. The resulting slurry was left over night. Then, the product was filtered off, washed three times with ethyl acetate (3×2 ml) and dried under vacuum at 40° C. yielding 2.3 g crystalline salt.

EXAMPLE 4

N-{2-tert-butyl-1-[(4,4-difluorocyclohexyl)methyl]-1H-benzimidazol-5-yl}ethanesulfonamide (101 mg) was dissolved in iso-propylacetate (1.5 ml) at 42° C. and ethane sulphonic acid (20 μl, 95%) was added. Crystallisation started immediately. The slurry was left for three days before it was filtered off and washed with iso-propylacetate (3×200 μl). The product was dried at 40° C. under vacuum to yield 61 mg crystalline N-{2-tert-butyl-1-[(4,4-difluorocyclohexyl)methyl]-1H-benzimidazol-5-yl}ethanesulfonamide esylate salt.

EXAMPLE 5

N-{2-tert-butyl-1-[(4,4-difluorocyclohexyl)methyl]-1H-benzimidazol-5-yl}ethanesulfonamide (111 mg) was slurried in methyl tert-butyl ether (2.1 ml) at 48° C. and ethane sulphonic acid (23 μl, 95%) was added. Shortly after the slurry became thinner and then recrystallised into a thicker slurry which was left over night at room temperature. The resulting crystals were filtered off, washed with methyl tert-butyl ether (2×400 μl) and dried at 40° C. under vacuum. A total of 105 mg (yield 75%) crystalline N-{2-tert-butyl-1-[(4,4-difluorocyclohexyl)methyl]-1H-benzimidazol-5-yl}ethanesulfonamide esylate was obtained.

EXAMPLE 6

N-{2-tert-butyl-1-[(4,4-difluorocyclohexyl)methyl]-1H-benzimidazol-5-yl}ethanesulfonamide (210 mg) was dissolved in methyl iso-butyl ketone (2.1 ml). A solution was made of ethansulphonic acid (43.7 μl) and methyl iso-butyl ketone (1.0 ml). The methyl iso-butyl ketone/ethane sulphonic acid solution was added in a controlled manner over three hours. Thus, initially, to the base solution was added 2×20 μl acid solution. Then after 30 minutes three more additions were made (3×20 μl). Approximately 20 minutes later three additions of 40 μl acid solution was made and after 40 minutes 400 μl was added. Finally, 20 minutes later the remaining amount of acid solution was added. The resulting slurry was left 2.5 days with stirring before it was filtered off and washed with methyl iso-butyl ketone (2×200 μl). The product was dried at 40° C. under vacuum yielding 227 mg crystalline N-{2-tert-butyl-1-[(4,4-difluorocyclohexyl)methyl]-1H-benzimidazol-5-yl}ethanesulfonamide esylate salt. (yield 85%)

EXAMPLE 7

N-{2-tert-butyl-1-[(4,4-difluorocyclohexyl)methyl]-1H-benzimidazol-5-yl}ethanesulfonamide (193 mg) was dissolved in iso-propyl acetate (3 ml) at 40° C. To the resulting clear solution ethane sulphonic acid (10 μl). was added. Crystallisation started immediately. After 50 minutes a second portion of acid was added (10 μl). Finally, after 10 minutes more a third portion of acid was added (10 μl). The slurry was left 2.5 days with stirring before it was filtered off and washed with iso-propylacetate (2×200 μl). The crystals were dried at 40° C. under vacuum. A total of 213 mg esylate salt was obtained which corresponds to a yield of approximately 87%.

The following NMR data were obtained from the ethane sulphonic acid salt of N-{2-tert-butyl-1-[(4,4-difluorocyclohexyl)methyl]-1H-benzimidazol-5-yl}ethanesulfonamide of Example 2.

$^1$HNMR (500 MHz, DMSO-$d_6$): 14.1 (1H, br), 10.2 (1H, br, s), 8.0 (1H, d), 7.7 (1H, split s), 7.4 (1H, split d), 4.5 (2H, d), 3.1 (2H, q), 2.4 (2H, q), 2.2 (1H, br t), 2.0 (2H, br t), 1.7 (4H, m), 1.6 (9H, s), 1.5 (2H, m), 1.2 (3H, t), 1.1 (3H, t)

The crystals of Example 3 were analyzed by XRPD and the results are tabulated below (Table 1) and are shown in FIG. 1.

TABLE 1

| d-value (Å) | Relative intensity |
|---|---|
| 14.0 | vs |
| 9.6 | vw |
| 9.2 | m |
| 8.4 | vw |
| 7.8 | s |
| 7.7 | s |
| 7.0 | s |
| 6.8 | m |
| 6.7 | s |
| 5.9 | w |
| 5.4 | m |
| 5.4 | w |
| 5.1 | w |
| 5.1 | m |
| 4.99 | vs |
| 4.77 | m |
| 4.62 | vs |
| 4.41 | s |
| 4.33 | m |
| 4.24 | s |
| 4.18 | m |
| 4.08 | m |
| 4.03 | m |
| 3.97 | w |
| 3.88 | m |
| 3.83 | m |
| 3.79 | m |
| 3.66 | m |
| 3.59 | vw |
| 3.50 | w |
| 3.44 | m |
| 3.40 | m |
| 3.31 | vw |
| 3.28 | m |
| 3.10 | m |
| 3.05 | m |
| 3.02 | m |
| 2.92 | w |
| 2.87 | w |
| 2.87 | w |
| 2.80 | w |
| 2.73 | w |
| 2.71 | w |
| 2.68 | vw |

The relative intensities are less reliable and instead of numerical values, the following definitions are used:

| % relative Intensity*: | Definition: |
|---|---|
| >80 | vs (very strong) |
| 37-80 | s (strong) |
| 9-37 | m (mediium) |
| 5-9 | w (weak) |
| <5 | vw (very weak) |

*the relative intensities are derived from the diffractograms measured with variable slits.

Preparation of Sulphuric Acid Salt of N-{2-tert-butyl-1-[(4,4-difluorocyclohexyl)methyl]-1H-benzimidazol-5-yl}ethanesulfonamide

EXAMPLE 8

N-{2-tert-butyl-1-[(4,4-difluorocyclohexyl)methyl]-1H-benzimidazol-5-yl}ethanesulfonamide (132 mg) was dissolved in ethyl acetate (1.2 ml) at 45° C. To the solution concentrated sulphuric acid was added (17 μl). Crystallisation started immediately. The temperature was increased shortly to 55° C. then cooled down to 20° C. and left over night. The crystals were filtered off, washed with ethyl acetate (1.0 ml), yielding 147 mg sulphate salt.

EXAMPLE 9

N-{2-tert-butyl-1-[(4,4-difluorocyclohexyl)methyl]-1H-benzimidazol-5-yl}ethanesulfonamide (139 mg) was dissolved in ethylacetat (2 ml) at room temperature. To the solution concentrated sulphuric acid was added (18 μl). The resulting slurry was evaporated to dryness and slurried in a mixture of ethanol (1.05 ml) and ethyl acetate (1.35 ml). The crystals were filtered off and dried, yielding 87 mg sulphate salt.

EXAMPLE 10

N-{2-tert-butyl-1-[(4,4-difluorocyclohexyl)methyl]-1H-benzimidazol-5-yl}ethanesulfonamide (177 mg) was dissolved in methyl iso-butyl ketone (1.8 ml). To the solution water (77 μl) and concentrated sulphuric acid (24 μl) was added. Initially, some oil formation was observed. After seeding, crystallisation started. The slurry was left over night. Then the crystals were filtered off, washed with methyl iso-butyl ketone (0.5 ml) and dried at 40° C. under vacuum. A total of 182 mg crystalline sulphate salt was isolated.

EXAMPLE 11

N-{2-tert-butyl-1-[(4,4-difluorocyclohexyl)methyl]-1H-benzimidazol-5-yl}ethanesulfonamide (104 mg) was dissolved in ethyl acetate (1.5 ml). To the solution water (40 μl) and concentrated sulphuric acid (13 μl) was added. Initially, some oil formation was observed. The solution was heated to 50° C. to initiate crystallisation. After 1 hour it was cooled down to room temperature. The slurry was left over night. Then the crystals were filtered off, washed with ethyl acetate (1 ml) and dried at 40° C. under vacuum. A total of 110 mg crystalline sulphate salt was isolated.

The following NMR data were obtained from the sulphuric acid salt of N-{2-tert-butyl-1-[(4,4-difluorocyclohexyl)methyl]-1H-benzimidazol-5-yl}ethanesulfonamide of Example 11:

$^1$HNMR (500 MHz, DMSO-$d_6$): 14.1 (1H, br s), 10.2 (1H, s), 8.0 (1H, d), 7.7 (1H, d), 7.4 (1H, dd), 4.5 (2H, d), 3.1 (2H, q), 2.2 (1H, m), 2.0 (2H, m), 1.7-1.8 (4H, m), 1.6 (9H, s), 1.5 (2H, m), 1.2 (3H, t)

Figure 2:
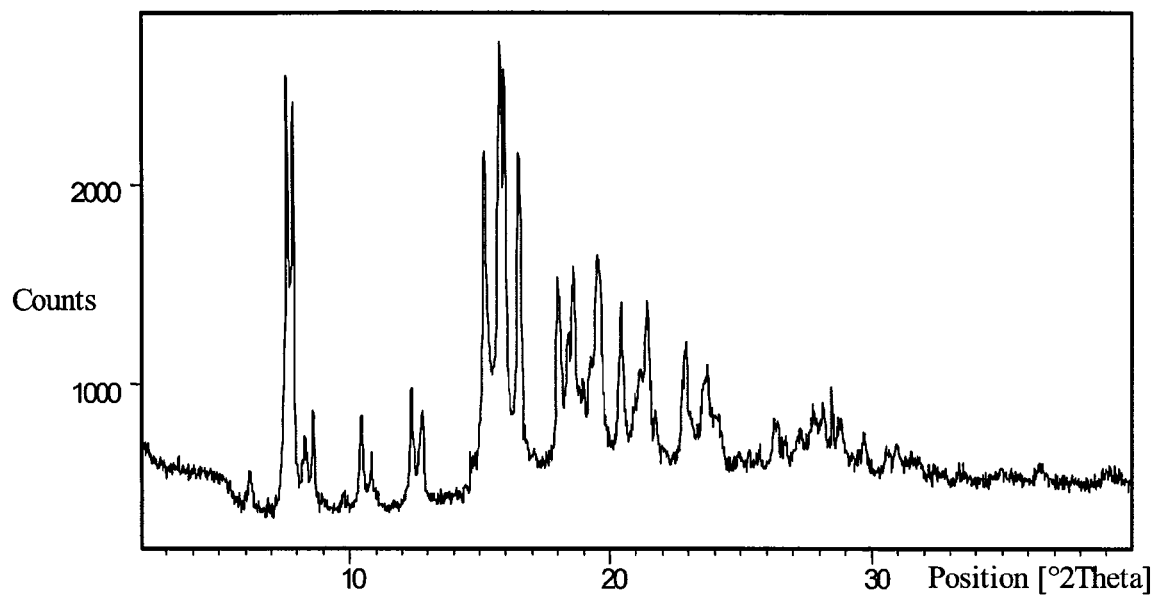
FIG. 2 shows an X-ray powder diffractogram for crystalline sulphuric acid salt of N-{2-tert-butyl-1-[(4,4-difluorocyclohexyl)methyl]-1H-benzimidazol-5-yl}ethanesulfonamide.

The crystals of Example 11 were analyzed by XRPD and the results are tabulated below (Table 2) and are shown in FIG. 2.

TABLE 2

| d-value (Å) | Relative intensity |
| --- | --- |
| 14.3 | w |
| 11.7 | s |
| 11.3 | s |
| 10.7 | w |
| 10.3 | m |
| 8.5 | m |
| 8.2 | w |
| 7.2 | m |
| 6.9 | m |
| 5.8 | s |
| 5.6 | s |
| 5.6 | s |
| 5.4 | s |
| 4.93 | m |
| 4.84 | m |
| 4.78 | m |
| 4.61 | m |
| 4.55 | m |
| 4.35 | m |
| 4.15 | m |
| 4.09 | w |
| 3.89 | m |
| 3.76 | m |
| 3.69 | w |
| 3.39 | w |
| 3.34 | w |
| 3.28 | w |
| 3.21 | w |
| 3.17 | w |
| 3.10 | w |
| 3.00 | w |
| 2.92 | w |
| 2.89 | w |

The relative intensities are less reliable and instead of numerical values, the following definitions are used:

| % relative Intensity*: | Definition: |
| --- | --- |
| >60 | s (strong) |
| 17-60 | m (mediium) |
| 5-17 | w (weak) |
| <5 | vw (very weak) |

*the relative intensities are derived from the diffractograms measured with variable slits.

Preparation of Ethane Disulphonic Acid Salt of N-{2-tert-butyl-1-[(4,4-difluorocyclohexyl)methyl]-1H-benzimidazol-5-yl}ethanesulfonamide

EXAMPLE 12

N-{2-tert-butyl-1-[(4,4-difluorocyclohexyl)methyl]-1H-benzimidazol-5-yl}ethanesulfonamide (21 mg) and 1,2-ethandisulphonic acid (13 mg) was dissolved in ethyl acetate (200 µl) at 40° C. After a few minutes crystallisation of the salt started. The slurry was cooled down and left at room temperature. The slurry was used as seeds in the following experiment.

EXAMPLE 13

N-{2-tert-butyl-1-[(4,4-difluorocyclohexyl)methyl]-1H-benzimidazol-5-yl}ethanesulfonamide (108 mg) was dissolved in ethyl acetate (1 ml). Then, 1,2-ethane disulphonic acid was added (49.5 mg). Crystallisation started immediately. The solution was seeded with a small amount of slurry from Example 11. Then, ethyl acetate was added (0.4 ml) and the slurry was left over night. The crystals were filtered off, washed with ethyl acetate (0.4 ml) and dried at 40° C. under vacuum. A total of 123 mg crystalline material was obtained.

Figure 3:
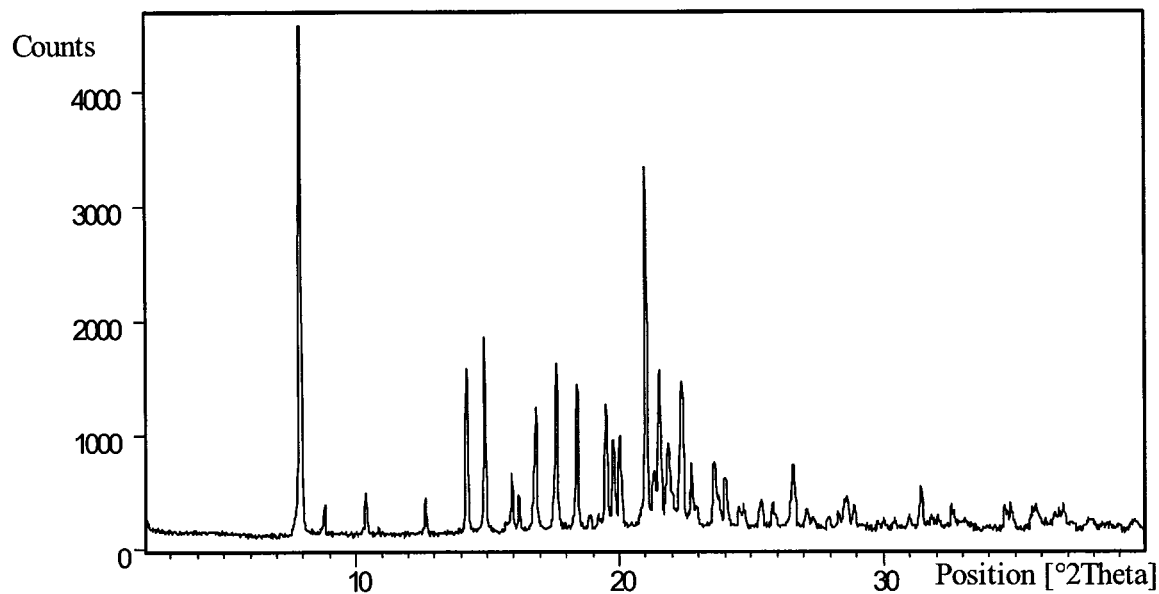
FIG. 3 shows an X-ray powder diffractogram for crystalline ethane disulphonic acid salt of N-{2-tert-butyl-1-[(4,4-difluorocyclohexyl)methyl]-1H-benzimidazol-5-yl}-ethanesulfonamide.

The crystals of Example 13 were analyzed by XRPD and the results are shown in FIG. 3.

Preparation of Maleic Acid salt of N-{2-tert-butyl-1-[(4,4-difluorocyclohexyl)methyl]-1H-benzimidazol-5-yl}ethanesulfonamide

EXAMPLE 14

N-{2-tert-butyl-1-[(4,4-difluorocyclohexyl)methyl]-1H-benzimidazol-5-yl}ethanesulfonamide (263 mg) was dissolved in ethyl acetate (2.5 ml) and water (60 µl). To the clear solution maleic acid was added (74.5 mg). The crystallisation started immediately and a thick slurry was obtained. The slurry was left over night before it was filtered off, washed with ethyl acetate (2×1 ml) and dried at 40° C. under vacuum. A total of 276 mg crystalline material was obtained.

Figure 4:
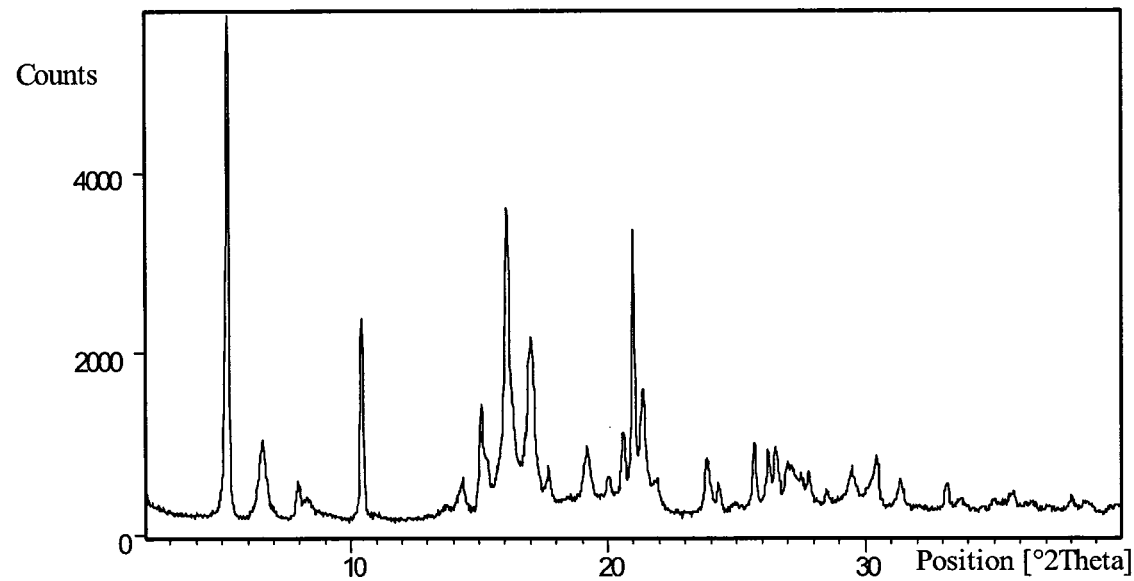
FIG. 4 shows an X-ray powder diffractogram for crystalline maleic acid salt of N-{2-tert-butyl-1-[(4,4-difluorocyclohexyl)methyl]-1H-benzimidazol-5-yl}ethanesulfonamide.

The crystals of Example 14 were analyzed by XRPD and the results are shown in FIG. 4.

Abbreviations

| | |
| --- | --- |
| br = | broad (in relation to NMR) |
| d = | doublet (in relation to NMR) |
| DCM = | dichloromethane |
| DMSO = | dimethylsulfoxide |
| dd = | doublet of doublets (in relation to NMR) |
| Et = | ethyl |
| h = | hour(s) |
| HCl = | hydrochloric acid |
| m = | multiplet (in relation to NMR) |
| Me = | methyl |
| min. = | minute(s) |
| MS = | mass spectroscopy |
| Pd/C = | palladium on carbon |
| q = | quartet (in relation to NMR) |
| rt = | room temperature |
| s = | singlet (in relation to NMR) |
| t = | triplet (in relation to NMR) |
| UV = | ultraviolet |

Prefixes n-, s-, i-, t- and tert- have their usual meanings: normal, secondary, iso, and tertiary.

The invention claimed is:

1. A salt of the compound N-{2-tert-butyl-1-[(4,4-difluorocyclohexyl)methyl]-1H-benzimidazol-5-yl}ethanesulfonamide, which is an ethanesuiphonic acid salt of said compound.

2. A salt of the compound N-{2-tert-butyl-1-[(4,4-difluorocyclohexyl)methyl]-1H-benzimidazol-5-yl}ethanesulfonamide, which is an ethanesulphonic acid salt of said compound, having an X-ray powder diffraction pattern with specific peaks at d-values at 14.0, 7.0, 4.99, and 4.62 Å.

3. A salt as claimed in claim 2 having an X-ray powder diffraction pattern with specific peaks at d-values at 14.0, 7.0, 4.99, and 4.62 Å, and as defined in Table 1 and as defined in FIG 1.

* * * * *